US011285172B2

(12) United States Patent
Wang et al.

(10) Patent No.: US 11,285,172 B2
(45) Date of Patent: Mar. 29, 2022

(54) METHOD FOR TREATING INFLAMMATORY DISEASES

(71) Applicants: MacKay Memorial Hospital, Taipei (TW); GoldRed NanoBiotech CO., LTD., Taoyuan (TW)

(72) Inventors: Hsueh-Hsiao Wang, New Taipei (TW); Hung-I Yeh, Taipei (TW); Hong-Shong Chang, Taoyuan (TW)

(73) Assignees: MacKay Memorial Hospital, Taipei (TW); GoldRed NanoBiotech CO., LTD., Taoyuan (TW)

( * ) Notice: Subject to any disclaimer, the term of this patent is extended or adjusted under 35 U.S.C. 154(b) by 149 days.

(21) Appl. No.: 16/799,855

(22) Filed: Feb. 25, 2020

(65) Prior Publication Data

US 2020/0268792 A1 Aug. 27, 2020

Related U.S. Application Data

(60) Provisional application No. 62/809,762, filed on Feb. 25, 2019.

(51) Int. Cl.

| *A61K 33/242* | (2019.01) |
| *A61K 9/51* | (2006.01) |
| *A61P 29/00* | (2006.01) |
| *A61K 9/00* | (2006.01) |
| *A61K 31/5415* | (2006.01) |
| *A61P 9/00* | (2006.01) |
| *A61K 45/06* | (2006.01) |
| *A61K 31/20* | (2006.01) |

(52) U.S. Cl.
CPC .......... *A61K 33/242* (2019.01); *A61K 9/5123* (2013.01); *A61P 29/00* (2018.01)

(58) Field of Classification Search
CPC .............. A61K 31/385; A61K 2300/00; A61K 33/242; A61K 31/20; A61K 31/352; A61K 31/365; A61K 31/4965; A61K 31/5415; A61K 33/24; A61K 45/06; A61K 9/0019; A61K 9/5115; A61K 9/5123; A61P 29/00; A61P 9/00
See application file for complete search history.

(56) References Cited

U.S. PATENT DOCUMENTS

| 9,101,672 B2* | 8/2015 | Yeh ..................... A61K 47/6923 |
| 2013/0052270 A1* | 2/2013 | Yeh ......................... A61P 39/06 |
| | | 424/498 |

OTHER PUBLICATIONS

Roux et al.; Langmuir (2005), 21, pp. 2526-2536. Published online Feb. 5, 2005.*
Lin et al., "Synthesis, Characterization, and Bioconjugation of Fluorescent Gold Nanoclusters toward Biological Labeling Applications", ACS Nano, vol. 3, No. 2, p. 395-401, 2009.

* cited by examiner

*Primary Examiner* — Jeffrey T. Palenik

(57) ABSTRACT

Disclosed herein is a method for treating an inflammatory disease in a subject, including administering to the subject a therapeutically effective amount of a dihydrolipoic acid (DHLA) coated gold nanocluster about 0.1 to 20 nm in diameter. Also disclosed is a method for reducing the expression of a pro-inflammatory molecule in a cultured cell, including contacting the cultured cell with the said DHLA coated gold nanocluster. Still disclosed is a pharmaceutical composition that includes the present DHLA coated gold nanocluster. The pharmaceutical composition is useful for treating the inflammatory disease in the subject.

14 Claims, 14 Drawing Sheets
(2 of 14 Drawing Sheet(s) Filed in Color)
Specification includes a Sequence Listing.

SEQUENCE LISTING

```
<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: Flt-1_sense

<400> SEQUENCE: 1
tctgaaatgg gtggctcttg a                                              21

<210> SEQ ID NO 2
<211> LENGTH: 22
<212> TYPE: DNA
<213> ORGANISM: Artificial Sequence
<220> FEATURE:
<223> OTHER INFORMATION: Flt-1_antisense

<400> SEQUENCE: 2
caactgcaga agtgctcatc ca                                             22

<210> SEQ ID NO 3
<211> LENGTH: 24
<212> TYPE: DNA
<213> ORGANISM: Artificial Sequence
<220> FEATURE:
<223> OTHER INFORMATION: VCAM-1_sense

<400> SEQUENCE: 3
cggattgctg ctcagattgg agac                                           24

<210> SEQ ID NO 4
<211> LENGTH: 23
<212> TYPE: DNA
<213> ORGANISM: Artificial Sequence
<220> FEATURE:
<223> OTHER INFORMATION: VCAM-1_antisense

<400> SEQUENCE: 4
aaactcacag ggctcagggt cag                                            23

<210> SEQ ID NO 5
<211> LENGTH: 21
<212> TYPE: DNA
<213> ORGANISM: Artificial Sequence
<220> FEATURE:
```

```
<223> OTHER INFORMATION: eNOS_sense

<400> SEQUENCE: 5
gcagcctcac tcctgttttc c                                              21

<210> SEQ ID NO 6
<211> LENGTH: 20
<212> TYPE: DNA
<213> ORGANISM: Artificial Sequence
<220> FEATURE:
<223> OTHER INFORMATION: eNOS_antisense

<400> SEQUENCE: 6
ttcactcgct tcgccatcac                                                20

<210> SEQ ID NO 7
<211> LENGTH: 21
<212> TYPE: DNA
<213> ORGANISM: Artificial Sequence
<220> FEATURE:
<223> OTHER INFORMATION: ICAM-1_sense

<400> SEQUENCE: 7
ctgaccccaa cccttgatga t                                              21

<210> SEQ ID NO 8
<211> LENGTH: 21
<212> TYPE: DNA
<213> ORGANISM: Artificial Sequence
<220> FEATURE:
<223> OTHER INFORMATION: ICAM-1_antisense

<400> SEQUENCE: 8
agccccattt gatcttttg c                                               21

<210> SEQ ID NO 9
<211> LENGTH: 19
<212> TYPE: DNA
<213> ORGANISM: Artificial Sequence
<220> FEATURE:
<223> OTHER INFORMATION: PAI-1_sense

<400> SEQUENCE: 9
gccgcctctt ccacaaatc                                                 19

<210> SEQ ID NO 10
<211> LENGTH: 21
<212> TYPE: DNA
<213> ORGANISM: Artificial Sequence
<220> FEATURE:
<223> OTHER INFORMATION: PAI-1_antisense

<400> SEQUENCE: 10
agcctggtca tgttgccttt c                                              21

<210> SEQ ID NO 11
<211> LENGTH: 20
<212> TYPE: DNA
<213> ORGANISM: Artificial Sequence
<220> FEATURE:
<223> OTHER INFORMATION: KDR_sense

<400> SEQUENCE: 11
gcaggaagta gccgcatttg                                                20
```

```
<210> SEQ ID NO 12
<211> LENGTH: 22
<212> TYPE: DNA
<213> ORGANISM: Artificial Sequence
<220> FEATURE:
<223> OTHER INFORMATION: KDR_antisense

<400> SEQUENCE: 12
gccattgctt gaagctcttt gt                                              22

<210> SEQ ID NO 13
<211> LENGTH: 20
<212> TYPE: DNA
<213> ORGANISM: Artificial Sequence
<220> FEATURE:
<223> OTHER INFORMATION: VEGF_sense

<400> SEQUENCE: 13
ctctacctcc accatgccaa                                                 20

<210> SEQ ID NO 14
<211> LENGTH: 20
<212> TYPE: DNA
<213> ORGANISM: Artificial Sequence
<220> FEATURE:
<223> OTHER INFORMATION: VEGF_antisense

<400> SEQUENCE: 14
gcatggtgat gttggactcc                                                 20

<210> SEQ ID NO 15
<211> LENGTH: 21
<212> TYPE: DNA
<213> ORGANISM: Artificial Sequence
<220> FEATURE:
<223> OTHER INFORMATION: P-selectin_sense

<400> SEQUENCE: 15
gaggctgaga actgggctga t                                               21

<210> SEQ ID NO 16
<211> LENGTH: 21
<212> TYPE: DNA
<213> ORGANISM: Artificial Sequence
<220> FEATURE:
<223> OTHER INFORMATION: P-selectin_antisense

<400> SEQUENCE: 16
tccttgtttg ctgcaggaca t                                               21

<210> SEQ ID NO 17
<211> LENGTH: 24
<212> TYPE: DNA
<213> ORGANISM: Artificial Sequence
<220> FEATURE:
<223> OTHER INFORMATION: vWF_sense

<400> SEQUENCE: 17
tgacagtgtt ccctattgga attg                                            24

<210> SEQ ID NO 18
<211> LENGTH: 20
<212> TYPE: DNA
<213> ORGANISM: Artificial Sequence
<220> FEATURE:
<223> OTHER INFORMATION: vWF_antisense
```

```
<400> SEQUENCE: 18
aggaaggaat tgcccaaggt                                              20

<210> SEQ ID NO 19
<211> LENGTH: 19
<212> TYPE: DNA
<213> ORGANISM: Artificial Sequence
<220> FEATURE:
<223> OTHER INFORMATION: TNF-alpha_sense

<400> SEQUENCE: 19
cctcctctct gccatcaag                                               19

<210> SEQ ID NO 20
<211> LENGTH: 18
<212> TYPE: DNA
<213> ORGANISM: Artificial Sequence
<220> FEATURE:
<223> OTHER INFORMATION: TNF-alpha_antisense

<400> SEQUENCE: 20
agtcggtcac ccttctcc                                                18

<210> SEQ ID NO 21
<211> LENGTH: 22
<212> TYPE: DNA
<213> ORGANISM: Artificial Sequence
<220> FEATURE:
<223> OTHER INFORMATION: SirT1_sense

<400> SEQUENCE: 21
ataggttagg tggtgaatat gc                                           22

<210> SEQ ID NO 22
<211> LENGTH: 21
<212> TYPE: DNA
<213> ORGANISM: Artificial Sequence
<220> FEATURE:
<223> OTHER INFORMATION: SirT1_antisense

<400> SEQUENCE: 22
ctgaagaatc tggtggtgaa g                                            21

<210> SEQ ID NO 23
<211> LENGTH: 22
<212> TYPE: DNA
<213> ORGANISM: Artificial Sequence
<220> FEATURE:
<223> OTHER INFORMATION: Beta-actin_sense

<400> SEQUENCE: 23
cctccctgga gaagagctac ga                                           22

<210> SEQ ID NO 24
<211> LENGTH: 20
<212> TYPE: DNA
<213> ORGANISM: Artificial Sequence
<220> FEATURE:
<223> OTHER INFORMATION: Beta-actin_antisense

<400> SEQUENCE: 24
cgccagacag cactgtgttg                                              20

<210> SEQ ID NO 25
<211> LENGTH: 18
```

```
<212> TYPE: DNA
<213> ORGANISM: Artificial sequence
<220> FEATURE:
<223> OTHER INFORMATION: IL-8_sense

<400> SEQUENCE: 25
ccactgtgcc ttggtttc                                                    18

<210> SEQ ID NO 26
<211> LENGTH: 21
<212> TYPE: DNA
<213> ORGANISM: Artificial sequence
<220> FEATURE:
<223> OTHER INFORMATION: IL-8_antisense

<400> SEQUENCE: 26
tcttgcacaa atatttgatg c                                                21

<210> SEQ ID NO 27
<211> LENGTH: 24
<212> TYPE: DNA
<213> ORGANISM: Artificial sequence
<220> FEATURE:
<223> OTHER INFORMATION: IL-1 beta_sense

<400> SEQUENCE: 27
tgatggctta ttacagtggc aatg                                             24

<210> SEQ ID NO 28
<211> LENGTH: 21
<212> TYPE: DNA
<213> ORGANISM: Artificial sequence
<220> FEATURE:
<223> OTHER INFORMATION: IL-1 beta_antisense

<400> SEQUENCE: 28
gtagtggtgg tcggagattc g                                                21
```

METHOD FOR TREATING INFLAMMATORY DISEASES

CROSS-REFERENCE TO RELATED APPLICATIONS

This application relates to and claims the benefit of U.S. Provisional Application No. 62/809,762, filed Feb. 25, 2019; the content of the application is incorporated herein by reference in its entirety.

BACKGROUND OF THE INVENTION

1. Field of the Invention

The present disclosure in general relates to the field of treating inflammatory diseases. More particularly, the present disclosure relates to methods of treating inflammatory diseases by use of a dihydrolipoic acid (DHLA) coated gold nanocluster that downregulates the expression of inflammatory-associated factors.

2. Description of Related Art

Cardiovascular disease (CCD) is an umbrella term for several linked pathologies that involve the heart or blood vessels and is the leading cause of death globally. Atherosclerosis, a condition developing when plaque builds up on artery walls, is the underlying mechanism of certain CCDs such as coronary heart disease (CHD), cerebrovascular disease, peripheral arterial disease (PAD), and stroke.

Recent studies suggest that inflammation plays roles in all stages of atherosclerosis. In general, the expression of pro-inflammatory molecules of endothelial cell linings at arterial luminal surface attracts inflammatory cells from the circulation into vascular wall and activates subsequent inflammation. The associated inflammatory factors and the immune responses work synergistically to accelerate arterial remodeling, thereby contributes to endothelial dysfunction and proceeds the development of atherosclerosis. In clinical, nonsteroidal anti-inflammatory drugs are widely used for reducing atherosclerosis, however the outcomes in treating cardiovascular diseases are inconsistent, not to mention their side effects that have been reported in recent years.

In view of the foregoing, there exists in the related art a need for an improved method for effectively reducing the expression and/or function of inflammatory molecules and/or cells thereby treating various inflammatory diseases (e.g., CCDs).

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method for treating an inflammatory disease in a subject. The method comprises administering to the subject an effective amount of a dihydrolipoic acid (DHLA) coated gold nanocluster. The DHLA coated gold nanocluster consists of a gold nanocluster formed by a plurality of gold nanoparticles, and a plurality of DHLAs coated on the gold nanocluster. According to embodiments of the present disclosure, the administration of the DHLA coated gold nanocluster reduces the expression of vascular endothelial growth factor (VEGF), intercellular adhesion molecule 1 (ICAM-1), vascular cell adhesion protein-1 (VACM-1), P-selectin, plasminogen activator inhibitor-1 (PAI-1), von Willebrand factor (vWF), tumor necrosis factor alpha (TNF-α), interleukin-8 (IL-8), and/or interleukin-1β (IL-1β) in the subject.

Also disclosed herein are the use of the DHLA coated gold nanocluster for the preparation of a medicament or a pharmaceutical composition to treat and/or prevent inflammatory diseases.

According to some embodiments of the present disclosure, the DHLA coated gold nanocluster is about 0.1 to 20 nm in diameter; preferably, about 1 to 2 nm in diameter.

Non-limiting examples of inflammatory diseases treatable with the present method, medicament or pharmaceutical composition includes, a cardiovascular disease, an inflammatory bowel disease, organ transplant rejection, lupus, an autoimmune disorder, a radiation-induced injury, cancer, a burn, trauma, a rheumatic disorder, a renal disease, an allergic disease, an infectious disease, an ocular disease, a skin disease, a gastrointestinal disease, a hepatic disease, cerebral edema, sarcoidosis, thrombocytopenia, and a spinal cord injury. According to one working example, the inflammatory disease is the cardiovascular disease.

In general, the cardiovascular disease may be any of angina pectoris, atheroma, atherosclerosis, arteriosclerosis, congestive heart failure, coronary heart disease, cardiomyopathy, myocardial infarction, stroke, ischemic condition, ischemic cardiomyopathy, patent ductus arteriosus, high blood pressure, pulmonary hypertension, peripheral artery disease, coronary artery disease, coronary artery spasm, or pericarditis.

Preferably, the subject is a human.

In some embodiments, the effective amount of the DHLA coated gold nanocluster is about 1 to 15 nM per day; preferably is about 3 to 12 nM per day; and more preferably is about 6 to 10 nM per day.

In some examples, the present method further comprises administering an endocytosis inhibitor concurrent with, or before the administration of the DHLA coated gold nanocluster.

Another aspect of the present disclosure pertains to a method for reducing the expression of a pro-inflammatory molecule in a cultured cell. The method comprises contacting the cultured cell with about 1 to 1000 nM of a dihydrolipoic acid (DHLA) coated gold nanocluster. The DHLA coated gold nanocluster consists of a gold nanocluster formed by a plurality of gold nanoparticles, and a plurality of DHLAs coated on the gold nanocluster. According to embodiments of the present disclosure, the pro-inflammatory molecule is selected from the group consisting of vascular endothelial growth factor (VEGF), intercellular adhesion molecule 1 (ICAM-1), vascular cell adhesion protein-1 (VACM-1), P-selectin, plasminogen activator inhibitor-1 (PAI-1), von Willebrand factor (vWF), tumor necrosis factor alpha (TNF-α), interleukin-8 (IL-8), and interleukin-1β (IL-1β).

According to some embodiments, the DHLA coated gold nanocluster is about 0.1 to 20 nm in diameter; preferably, about 1 to 2 nm in diameter.

The cultured cell may be a human aortic endothelial cell (HAEC), human epithelial cell, human coronary artery endothelial cell (HCAEC), or human endothelial progenitor cell (HEPC).

Alternatively or optionally, the cultured cell may be further treated by an endocytosis inhibitor.

By the virtue of the above features, the DHLA coated gold nanoclusters of the disclosure have high biocompatibility in specific cardiovascular cell lines via clathrin-mediated endocytosis. In addition, since long-term incubation of DHLA coated gold nanoclusters lowers the expression of certain pro-inflammatory molecules, such as angiogenic growth factors, adhesion molecules, coagulator factors and even inflammatory cytokines, the treatment via administering the DHLA coated gold nanoclusters has anti-inflammatory, anti-atherothrombosis and anti-atherosclerosis effects.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where:

FIG. 1D: Representative images of FANC uptake post treatment with endocytosis inhibitors. Chlor, chlorpromazine hydrochloride. *, $P<0.05$; **, $P<0.01$, compared to pure FANCs control group. Scale bar, 10 μm.

FIG. 2A: Duration of 21 days; FIG. 2B: Duration of 28 days. Values are mean±SD of triplicate assays from 3 independent experiments. *, $P<0.05$, compared to control group.

FIG. 4A: The representative confocal images of THP-1 cells attaching to HAECs. FIG. 4B: The quantification data of each experimental group. Values are mean±SD of triplicate assays from 3 independent experiments. *, $P<0.05$.

DETAILED DESCRIPTION OF THE INVENTION

Figure 1A:
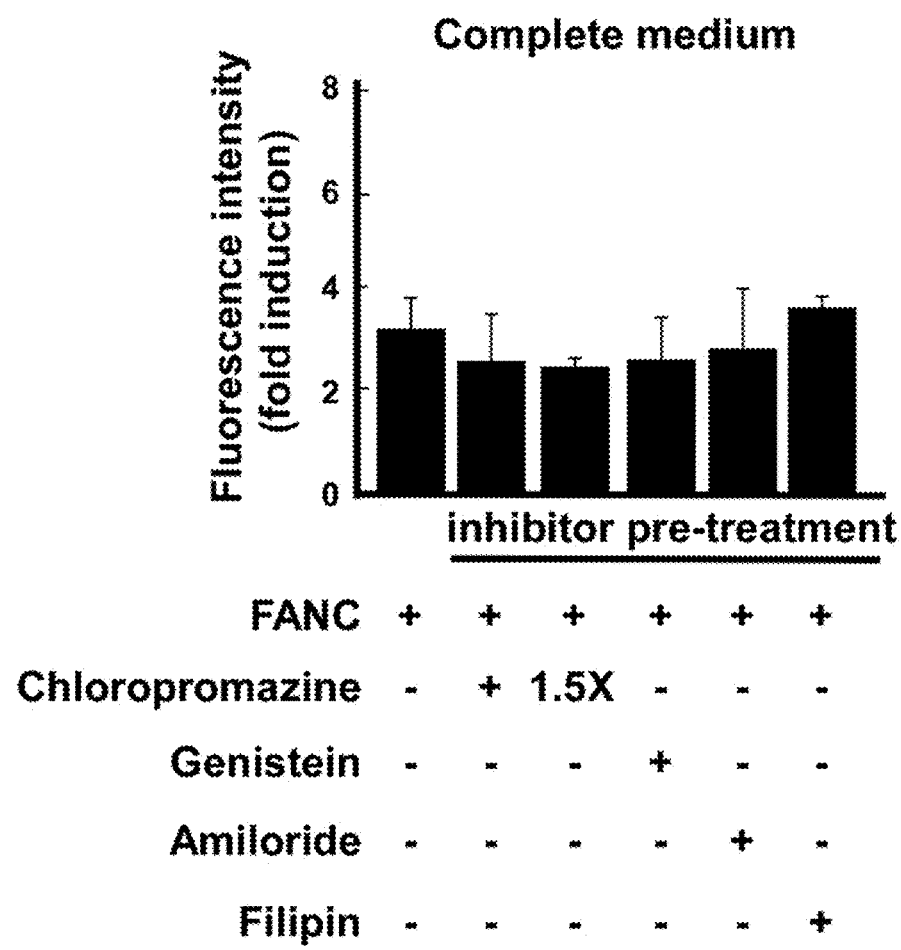
FIGS. 1A-1D are the data depicting the effect of endocytosis inhibitors on DHLA coated gold nanoclusters (indicated as "FANC" in figures) internalization. After inhibitors pre-treatment in defined medium, the medium was replaced with FANC-containing medium for additional 80 minutes and subject to flow cytometry analysis (FIGS. 1A-1C). Note that chlorpromazine hydrochloride attenuated FANC internalization in a dose-dependent manner only in low serum and no serum supplement culture environments.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "an effective amount" as used herein refers to the quantity of the gold nanoclusters which is sufficient to yield a desired response. For in vitro application, such as reducing the inflammation of a cultured cell, the specific effective amount will vary with factors such as the type of cells that contacts with the gold nanoclusters, or the number of passages that the cells have been through. Effective amount may be expressed, for example, as the concentration of the gold nanoclusters being applied, the total mass of the gold nanoclusters (e.g., in grams, milligrams or micrograms; in mole, millimole, micromole, or nanomole), a ratio of the total mass of the gold nanoclusters to the total volume of the cultured medium (e.g., as milligrams per kilogram (mg/kg) or nanomole per liter (nM)). Preferably, the gold nanoclusters are applied in a concentration of about 1 to 1,000 nM; more preferably in a concentration of about 10 to 500 nM; and even more preferably in a concentration of about 30 to 150 nM. For in vivo application, such as reducing inflammation responses and/or treating an inflammatory disease of a subject, the specific effective amount will vary with factors such as the particular condition being treated, the physical condition of the subject (e.g., the subject's body mass, age, or gender), the type of mammal or animal being treated, the duration of the treatment, the nature of concurrent therapy (if any), and the specific formulations employed. Preferably, the effective amount of the present gold nanoclusters is applied to a subject (e.g., human) in a nanomolar concentration of about 1 to 15 nM; more preferably in a nanomolar concentration of about 3 to 12 nM; and even more preferably in a nanomolar concentration of 6 to 10 nM.

The term of "inflammatory disease," "inflammatory disorder" or "inflammatory condition" refers to any disease marked by inflammation, which may be caused by a multitude of inciting events, including radiant, mechanical, chemical, infections, and immunological stimuli. Inflammatory conditions can be identified via clinical and pathological features, and/or expression of well-known inflammatory-related molecules secreted by tissues and/or cells. Inflammatory diseases can refer to any diseases in which inflammation conditions present. Examples of inflammatory diseases include, but are not limited to, cardiovascular diseases, arthritis, inflammatory bowel disease, asthma, psoriasis, organ transplant rejection, radiation-induced injuries, cancer, lupus, burns, trauma, rheumatic disorder, renal diseases, allergic diseases, infectious diseases, ocular diseases, skin diseases, gastrointestinal diseases, hepatic diseases, cerebral edema, sarcoidosis, thrombocytopenia, spinal cord injuries, and autoimmune disorders.

The term "cardiovascular disease" or "cardiovascular inflammation-related disease" as used herein refers to any disease or disorder of the heart or blood vessels (i.e. arteries and veins) or any symptom thereof, especially encompassing inflammation condition. Examples of said diseases include but are not limited to, acute and chronic cardiovascular inflammation including as a result of surgery or other trauma, a cardiovascular disease, angina pectoris, atheroma, atherosclerosis, arteriosclerosis, congestive heart failure, coronary heart disease, cardiomyopathy, myocardial infarction, stroke, ischemic conditions, ischemic cardiomyopathy, hypertriglyceridemia, hypercholesterolemia, patent ductus arteriosus, high blood pressure, myocardial infarction, pulmonary hypertension, peripheral artery disease, coronary artery disease, coronary artery spasm, pericarditis, Wegener's granulomatosis, Takayasu's arteritis, Kawasaki syndrome, anti-factor VIII autoimmune disease, necrotizing small vessel vasculitis, microscopic polyangiitis, and Churg-Strauss syndrome.

The term "pro-inflammatory molecules" refers to molecules that can promote inflammation in organism and/or in cultured cell lines. Generally, the pro-inflammatory molecules include growth factors, adhesion molecules, coagulation factors and inflammatory cytokines. In many instances, adhesion molecules play a crucial role in inflammation by expressing on the endothelial walls, so as to stimulate monocytes infiltrate. On the other hand, lymphocytes in immune systems can participate in the regulation of pro-inflammatory molecules (e.g., cytokines) by the production of anti-inflammatory molecules thereof. The pro-inflammatory molecules show down-regulation under occurrence of substances or agents encompassing anti-inflammatory ability.

The term "endocytosis inhibitor" refers to molecules that inhibits endocytic pathways, regardless the mediation of endocytosis mechanism. The endocytosis typically includes pinocytosis, which might be mediated by clathrin, and phagocytosis, which involves the internalization of enlarged fluid-filled endosomes. Examples of the said endocytosis inhibitor include but are not limited to, clathrin-dependent inhibitors, such as chlorpromazine hydrochloride and amiloride; and non-clathrin inhibitors, such as genistein and filipin.

The term "coagulation factor" refers to any molecules or proteins that be involved in the coagulation process by which the blood changes from a liquid to a gel, forming a blood clot.

II. Description of the Invention

The present disclosure is based, at least in part, on the discovery that the DHLA coated gold nanocluster is useful in reducing the expression of several inflammation-associated molecules thereby providing a potential means to prevent and/or treat inflammatory diseases In structure, each DHLA coated gold nanocluster consists of a gold nanocluster formed by a plurality of gold nanoparticles, and a plurality of DHLA coated on the gold nanocluster. The DHLA coated gold nanoclusters used in the present disclosure are known to the skilled practitioner as well as the process for their production (Lin et al., *ACS Nano* 2009, 3 (2), pp 395-401); hence the further details are omitted herein for the sake of brevity. The DHLA coated gold nanoclusters have a fluorescent emission at 650 nm under an excitation wavelength at approximately 420 nm, hence the emission is in the range of red to near infrared light. Each DHLA coated gold nanocluster has a particle size of 0.1 to 20 nm, more preferably the particle size of 1 to 15 nm, and even more preferably the particle size of 1.3 to 3.4 nm. The dimension discussed above related to the gold nanocluster of the present disclosure is in dried state, however, it is of advantage if the gold nanocluster used in the present disclosure is water-soluble or at least dispersible in aqueous medium and/or water, the hydrodynamic size of the gold nanocluster of the present disclosure can be significantly larger than the dried size due to the coupling of surrounding solvent molecule, such as water. In one specific embodiment example, the gold nanocluster has a hydrodynamic size corresponds to 1 to 30 kDa polyethylene glycol (PEG) molecules as size standard (Lin et al., *ACS Nano* 2009, 3 (2), pp 395-401).

According to one aspect, the DHLA coated gold nanoclusters are useful for reducing the expression of at least one pro-inflammatory molecule in cultured cells. In certain embodiments, the cultured cells are contacted with the DHLA coated gold nanoclusters in a concentration from about 1 to 1,000 nM for a period of time, such as from 1 to 10 hours, more preferably from 3 to 7 hours, and even more preferably from 4 to 6 hours. According to embodiments of the present disclosure, the pro-inflammatory molecules reduced by the present DHLA coated gold nanoclusters include, but are not limited to, growth factors, adhesion molecules, and coagulation factors.

Non-limited example of growth factors includes vascular endothelial growth factor (VEGF), fibroblast growth factor (FGF), platelet-derived growth factor (PDGF), hepatocyte growth factor (HGF), epidermal growth factor (EGF), transforming growth factor-α (TGF-α), basic and acidic fibroblast growth factors, connective tissue growth factor (CTGF), and/or Heparin-binding EGF-like growth factor (HB-EGF). In certain embodiments, the growth factor is VEGF.

Examples of adhesion molecules incudes, but are not limited to, intercellular adhesion molecule 1 (ICAM-1), vascular cell adhesion protein-1 (VACM-1), E-selectin, and/or P-selectin. In certain embodiments, the adhesion molecule is selected from the group consisting of ICAM-1, VACM-1, and P-selectin.

Examples of coagulation factors include, but are not limited to, coagulation factors I to XIII, von Willebrand factor (vWF), heparin cofactor II, plasminogen activator inhibitor-1 (PAI-1), and/or plasminogen activator inhibitor-2 (PAI2). In certain embodiments, the coagulation factor includes vWF and PAI-1.

In some optional or alternative embodiments, the DHLA coated gold nanoclusters also reduce the expression of inflammatory cytokines. In some embodiments, the inflammatory cytokines include interleukin-1 family (IL-1), IL-12, and IL-18, tumor necrosis factor (TNF), interferon γ (IFN-γ), and/or granulocyte-macrophage colony stimulating factor. In certain embodiments, the DHLA coated gold nanoclusters inhibit the overexpression of IL-1 family and TNF family.

The cultured cells treatable by the DHLA coated gold nanoclusters of the present disclosure include, but are not limited to, human aortic endothelial cell (HAEC), human epithelial cell, human coronary artery endothelial cell (HCAEC), and human endothelial progenitor cell (HEPC). In some embodiments, the cultured cells are HAECs.

In another aspect, the present disclosure is directed to the use of the DHLA coated gold nanocluster for manufacturing a pharmaceutical composition and/or medicament for treating an inflammatory disease in a subject. The pharmaceutical composition or said medicament comprises an effective amount of the DHLA coated gold nanocluster of the present disclosure; and optionally, a pharmaceutically acceptable excipient. Suitable pharmaceutically acceptable excipients include Water-for-Injection, 0.9% saline, and/or 5% glucose solution, but not limited thereto.

Non-limited examples of the inflammatory disease treatable by the present pharmaceutical composition or said medicament include, but are not limited to, a cardiovascular disease, an inflammatory bowel disease, organ transplant rejection, lupus, an autoimmune disorder, a radiation-induced injury, cancer, a burn, trauma, a rheumatic disorder, a renal disease, an allergic disease, an infectious disease, an ocular disease, a skin disease, a gastrointestinal disease, a hepatic disease, cerebral edema, sarcoidosis, thrombocytopenia, and a spinal cord injury.

Further, the cardiovascular disease may be any of angina pectoris, atheroma, atherosclerosis, arteriosclerosis, congestive heart failure, coronary heart disease, cardiomyopathy, myocardial infarction, stroke, ischemic condition, ischemic cardiomyopathy, patent ductus arteriosus, high blood pressure, pulmonary hypertension, peripheral artery disease, coronary artery disease, coronary artery spasm, or pericarditis.

The pharmaceutical composition or medicament of the present disclosure is useful in reducing the expression of pro-inflammatory molecules, such as VEGF, ICAM-1, VACM-1, P-selectin, PAI-1, and vWF in the subject, thus may be useful for treating the inflammatory disease, and/or ameliorating or alleviating the symptoms associated with the inflammatory disease. Optionally or additionally, the pharmaceutical composition or said medicament as described herein can reduce the overexpression of inflammatory cytokines, such as IL-1 family and TNF family.

In certain embodiments, the DHLA coated gold nanoclusters described herein are provided in an effective amount in the pharmaceutical composition. In certain embodiments, the effective amount is a therapeutically effective amount (e.g., amount effective for treating inflammation and/or reducing expression of pro-inflammatory molecules). In certain embodiments, the effective amount is a prophylactically effective amount (e.g., amount effective for preventing inflammatory conditions in a subject in need thereof).

Pharmaceutical compositions described herein can be prepared by any method known in the art of pharmacology. For application of the present invention, the DHLA coated gold nanoclusters of the present disclosure are manufactured into usual formulations such as tablets, sugar-coated tablets, pills, granules, aerosols, syrups, emulsions, suspensions, solutions, ointments, creams or gels or any kind, by using inert, essentially nontoxic, pharmaceutically suitable carriers or solvents. Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient (e.g., the DHLA coated gold nanoclusters of the present disclosure).

In certain embodiments, the composition is a pharmaceutical composition. In certain embodiments, the composition is a nutraceutical composition. In certain embodiments, the composition is a health food. In some embodiments, the compositions described herein can be a health food or health food product, which can be any kinds of liquid and solid/semi-solid materials that are used for nourishing humans and animals, for benefiting treatment of an inflammatory disease and/or ameliorating or alleviating the symptoms associated with the inflammatory disease. The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The DHLA coated gold nanoclusters provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

In another aspect, the present disclosure provides a method for treating inflammatory diseases in a subject. The method comprises administering to the subject an effective amount of a DHLA coated gold nanocluster, or a composition comprising such, as described.

In some embodiments, the inflammatory disease treatable by the DHLA coated gold nanocluster include, but are not limited to, cardiovascular diseases, inflammatory bowel diseases, organ transplant rejection, lupus, autoimmune disorders, radiation-induced injuries, cancer, burns, trauma, rheumatic disorder, renal diseases, allergic diseases, infectious diseases, ocular diseases, skin diseases, gastrointestinal diseases, hepatic diseases, cerebral edema, sarcoidosis, thrombocytopenia, and spinal cord injuries.

In some embodiments, the inflammatory condition is related to the progression of cardiovascular diseases in which inflammation responses are involved. Examples of the cardiovascular diseases include, but are not limited to, angina pectoris, atheroma, atherosclerosis, arteriosclerosis, congestive heart failure, coronary heart disease, cardiomyopathy, myocardial infarction, stroke, ischemic conditions, ischemic cardiomyopathy, patent ductus arteriosus, high blood pressure, pulmonary hypertension, peripheral artery disease, coronary artery disease, coronary artery spasm, and pericarditis.

In other embodiments, the administration of the DHLA coated gold nanocluster reduces the expression of inflammation-associated adhesion molecules as described herein, such as VEGF, ICAM-1, VACM-1, P-selectin, PAI-1, and vWF. In some optional or additional embodiments, the DHLA coated gold nanocluster is administered to the subject to reduce the expression of inflammatory cytokines, including but are not limited to, IL-1, IL-12, IL-18, TNF, IFN-γ, and/or granulocyte-macrophage colony stimulating factor.

The DHLA coated gold nanocluster and compositions comprising such provided herein can be administered by any suitable route, including enteral (e.g., oral), parenteral, intravenous, intramuscular, intra-arterial, intramedullary, intrathecal, subcutaneous, intraventricular, transdermal, interdermal, subcutaneous, intradermal, rectal, intravaginal, intraperitoneal, topical (as by powders, ointments, creams, and/or drops). Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of DHLA coated gold nanoclusters required to achieve an effective amount will vary from subject to subject, depending, for example, on species, age, and general condition of a subject, severity of the side effects or disorder, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of DHLA coated gold nanoclusters described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every other week, one dose monthly or one dose every other month. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, a dose (e.g., a single dose, or any dose of multiple doses) described herein includes DHLA coated gold nanoclusters of the present disclosure that is independently about 1 to 15 nM per kilogram of body weight per day, in particular about 3 to 12 nM per kilogram of body weight per day, preferably about 6 to 10 nM per kilogram of body weight per day. In one preferred embodiment, the dose including an effective amount is about 8.1 nM per kilogram of body weight per day.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A DHLA coated gold nanocluster or a composition comprising such, as described herein, can be administered in combination with one or more additional pharmaceutical agents (e.g., therapeutically and/or prophylactically active agents) useful in treating, reducing the risk for, or delaying the onset of any of the inflammatory diseases/conditions as described herein. The DHLA coated gold nanocluster or the composition comprising such can be administered in combination with the additional pharmaceutical agents that improve their activity (e.g., activity in treating and/or reducing the inflammatory conditions in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a DHLA coated gold nanocluster described herein and an additional pharmaceutical agent shows a synergistic effect that is absent in a pharmaceutical composition including either DHLA coated gold nanocluster or the additional pharmaceutical agent.

In some embodiments, the additional pharmaceutical agent may be an endocytosis inhibitor, which includes chlorpromazine hydrochloride, filipin, amiloride, and genistein. In some embodiments, the endocytosis inhibitor is administered before administering the DHLA coated gold nanocluster. In other embodiments, the endocytosis inhibitor and the DHLA coated gold nanocluster are administered simultaneously.

In some embodiments, the subject is mammal, preferably is human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

DHLA Coated Gold Nanocluster (FANG) Synthesis and Cultured Cell Preparation

Human aortic endothelial cells (HAECs) were maintained in endothelial cell growth medium (MV) with 5% fetal bovine serum (FBS) and endothelial cell growth supplement (annotated complete medium hereinafter; both obtained from PromoCell, Heidelberg, Germany). HAECs were cultured in the complete medium maintained under 37° C. in a humidified incubator in an atmosphere of 5% $CO_2$-95% air and serially passaged twice a week. DHLA coated gold nanoclusters used in this study were prepared based on precursor-induced gold (Au) nanoparticle (NP) etching (Lin et al., ACS Nano, 2009, 3 (2), pp 395-401). Briefly, 6-nm gold nanoparticles stabilized with didodecyldimethylammonium bromide (DDAB) were firstly synthesized in toluene via adding 0.8 ml gold precursors ($AuCl_3$, 7.5 mg/ml prepared in 100 mmol/L DDAB solution) into the reduction agents containing 1 ml of fresh-prepared tetrabutylammonium borohydride (TBAB) (100 mmol/L in DDAB solution) as well as 0.675 ml decanoic acid (100 mmol/L in toluene).

Additional gold precursors were dropwise added until the color changed to transparent yellow, resulting in non-plasmonic gold nanoclusters which can be further brought to aqueous phase upon ligand exchange with reduced α-lipoic acid. α-lipoic acid (0.206 g, Sigma-Aldrich, St. Louis, Mo., USA) was reduced into dihydrogenliopic acid (DHLA) by adding 5 ml TBAB (50 mmol/L) in DDAB solution. DHLA coated gold nanoclusters were formed by mixing equal amount of gold precursors with DHLA and being subjected to additional UV light (302 nm) annealing for 30 minutes, resulting in the stable fluorescence signal in living cells. For the sake of brevity, the DHLA coated gold nanocluster is abbreviated as "FANC".

After removing the supernatants by centrifugation, FANC were further purified by following methanol/chloroform washing steps and redisposed in borate buffer (pH 9) for overnight incubation under 55° C., and collected and buffer-exchanged by centrifugal filter between 30-100 kDa (EMD Millipore).

Endocytic Pathway Inhibition

In certain experiments, HAECs were treated by endocytosis inhibitors to inhibit endocytic pathways. Endocytosis inhibitors are chlorpromazine hydrochloride (10 μg/ml, C8138), filipin (10 μg/ml, F9765), amiloride (10 μmol/L A7410), and genistein (50 μmol/L G6649; all obtained from Sigma-Aldrich).

Immunofluorescence

Cells were seeded onto 2% gelatin-coated glass coverslips and incubated for 24 hours and applied to FANCs treatments. Cells were fixed with 1% paraformaldehyde, washed with PBS, then blocked with 5% bovine serum albumin (BSA) for 30 minutes. Then the cell culture was incubated with primary antibodies against VE-cadherin at 37° C. for 2 hours, followed by application of FITC-conjugated secondary antibody (Chemicon, Temecula, Calif., USA) for 50 minutes under room temperature. After one hour for the pre-treatment by above-mentioned endocytosis inhibitor, HAECs were incubated with FANCs for 80 minutes followed by washed with PBS and fixed with 1% paraformaldehyde. Afterwards, cells were stained with bisbenzamide (18.7 μmol/L) for 15 minutes and then washed with PBS buffer. Then, the cells were mounted by using 60% glycerol (v/v) and examined by using a confocal microscope (Leica TCS SP5, Leica, Germany) with a 40× oil objective/1.25 aperture. The images were captured under room temperature.

Real-Time PCR

After treating with DHLA coated gold nanoclusters, contaminated medium was replaced with fresh culture medium. Total RNA from cells were extracted using RNeasy Plus mini kit (Qiagen, Hilden, Germany) at indicated time points. RNA (2 μg) was applied to the reaction of reverse transcription using First-Strand Synthesis System kit (BioRad, Hercules, Calif., USA). The cDNA products (0.5 μl) was used for quantitative PCR amplification with specific primers for vascular endothelial growth factor (VEGF), vascular endothelial growth factor receptor 1 (Flt-1), vascular endothelial growth factor receptor 2 (KDR), vascular cell adhesion molecule 1 (VCAM-1), intercellular cell adhesion molecule 1 (ICAM-1), P-selectin, plasminogen activator inhibitor-1 (PAI-1), von Willebrand factor (vWF), endothelial nitric oxide synthase (eNOS), sirtuin 1 (SirT1), tumor necrosis factor alpha (TNF-α), interleukin-8 (IL-8), interleukin-1β (3 (IL-1β), and β-actin (sequences are listed in Table 1). To conduct real-time PCR, iQ™ SYBR® Green Supermix reagent and MyiQ Single-Color Real-Time PCR Detector System (both obtained from Bio-Rad, Calif., USA) were used. Relative mRNA levels were normalized with the corresponding levels of (β-actin. At least 3 independent experiments were performed for analysis.

TABLE 1

The sequence of primers used in real-time PCR

| Gene | Primer | Sequence (5'-3') | SEQ NO |
|---|---|---|---|
| Flt-1 | Sense | TCTGAAATGGGTGGCTCTTGA | 1 |
| | Antisense | CAACTGCAGAAGTGCTCATCCA | 2 |
| VCAM-1 | Sense | CGGATTGCTGCTCAGATTGGAGAC | 3 |
| | Antisense | AAACTCACAGGGCTCAGGGTCAG | 4 |
| eNOS | Sense | GCAGCCTCACTCCTGTTTTCC | 5 |
| | Antisense | TTCACTCGCTTCGCCATCAC | 6 |
| ICAM-1 | Sense | CTGACCCCAACCCTTGATGAT | 7 |
| | Antisense | AGCCCCATTTGATCTTTTTGC | 8 |
| PAI-1 | Sense | GCCGCCTCTTCCACAAATC | 9 |
| | Antisense | AGCCTGGTCATGTTGCCTTTC | 10 |
| KDR | Sense | GCAGGAAGTAGCCGCATTTG | 11 |
| | Antisense | GCCATTGCTTGAAGCTCTTTGT | 12 |
| VEGF | Sense | CTCTACCTCCACCATGCCAA | 13 |
| | Antisense | GCATGGTGATGTTGGACTCC | 14 |
| P-Selectin | Sense | GAGGCTGAGAACTGGGCTGAT | 15 |
| | Antisense | TCCTTGTTTGCTGCAGGACAT | 16 |
| vWF | Sense | TGACAGTGTTCCCTATTGGAATTG | 17 |
| | Antisense | AGGAAGGAATTGCCCAAGGT | 18 |
| TNF-α | Sense | CCTCCTCTCTGCCATCAAG | 19 |
| | Antisense | AGTCGGTCACCCTTCTCC | 20 |
| SirT1 | Sense | ATAGGTTAGGTGGTGAATATGC | 21 |
| | Antisense | CTGAAGAATCTGGTGGTGAAG | 22 |
| β-actin | Sense | CCTCCCTGGAGAAGAGCTACGA | 23 |
| | Antisense | CGCCAGACAGCACTGTGTTG | 24 |
| IL-8 | Sense | CCACTGTGCCTTGGTTTC | 25 |
| | Antisense | TCTTGCACAAATATTTGATGC | 26 |
| IL-1β | Sense | TGATGGCTTATTACAGTGGCAATG | 27 |
| | Antisense | GTAGTGGTGGTCGGAGATTCG | 28 |

Cell Adhesion Assay

HAECs ($7.5 \times 10^4$ cells) were grown in 6-well plates at 37° C. HAECs were treated with different concentrations (50 and 100 nM) of FANC for 72 hours at 37° C. and then activated with LPS (100 ng/ml) overnight. Before performing cell adhesion assay, cells were washed three times with Hank's Balanced Salt Solution (HBSS) containing 0.1% BSA. THP-1 cells were suspended at a density of $1.0 \times 10^6$ cells/ml of 0.1% BSA/HBSS and labeled with 1 μM of Calcein-AM (Biotium, Hayward, Calif.) by 60-minutes incubation at 37° C., followed by three washes of 0.1% BSA/HBSS. Labeled THP-1 cells were then incubated with HAECs for 2 hours at 37° C. Non-adherent cells were washed out carefully by 0.1% BSA/HBSS for 3 times. The attached Calcein-AM labeled THP-1 cells on HAECs were quantified manually under a fluorescence microscope (DM IRBE; Leica).

Animals and Treatments

Male adult (12 weeks) C57B/6 mice were intraperitoneally injected with FANC (100 nM) and/or LPS (10 mg/Kg) (N=3 for each group). After 2 hours treatment, animals were sacrificed and sera were harvested. Equal amount of sera (35 μL) from each animal were pooled together and incubated with antibody pre-printed membranes (Mouse Cytokine Array Panel A, ARY006, R&D systems, USA). The positive signals appeared on developed membranes were detected and quantified. Corresponding signals on different arrays were compared to determine the relative change in cytokine level among groups.

Electron Microscopy

For thin-section electron microscopy, cultured cells were fixed with 2.5% glutaraldehyde in 0.1 mol/L phosphate buffer (pH 7.2) for 1 hour. The specimens were then rinsed in PBS buffer, post-fixed in phosphate-buffered osmium (VIII) oxide (1%), dehydrated in ethanol and embedded with Spurr's resin. Thin sections were stained with uranyl acetate and lead citrate, then examined with a transmission electron microscope (JEM-1200EXII, JEOL, Mass., USA).

Data Analysis

Experiment results expressed as mean±SD, were analyzed using one-way ANOVA or Student's t-test. Consider the data are statistically significant when P value<0.05.

Figure 1B:
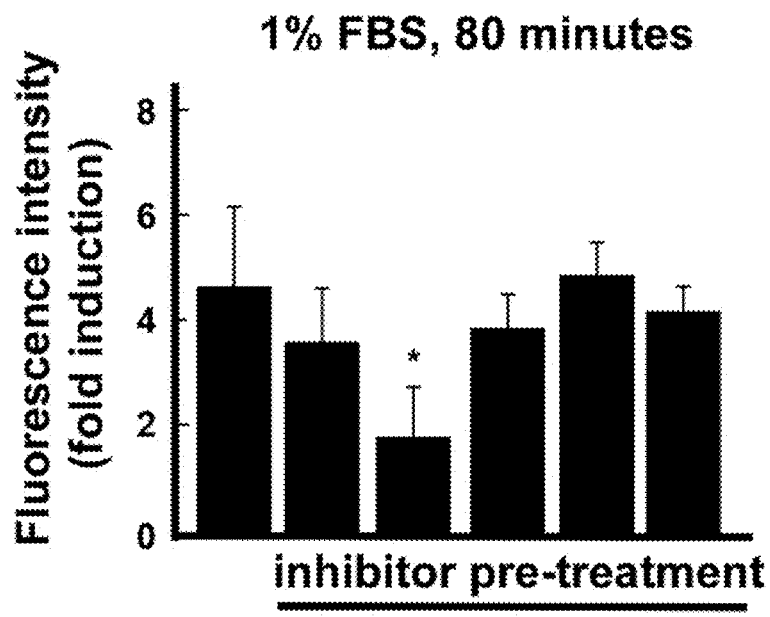
Figure 1C:
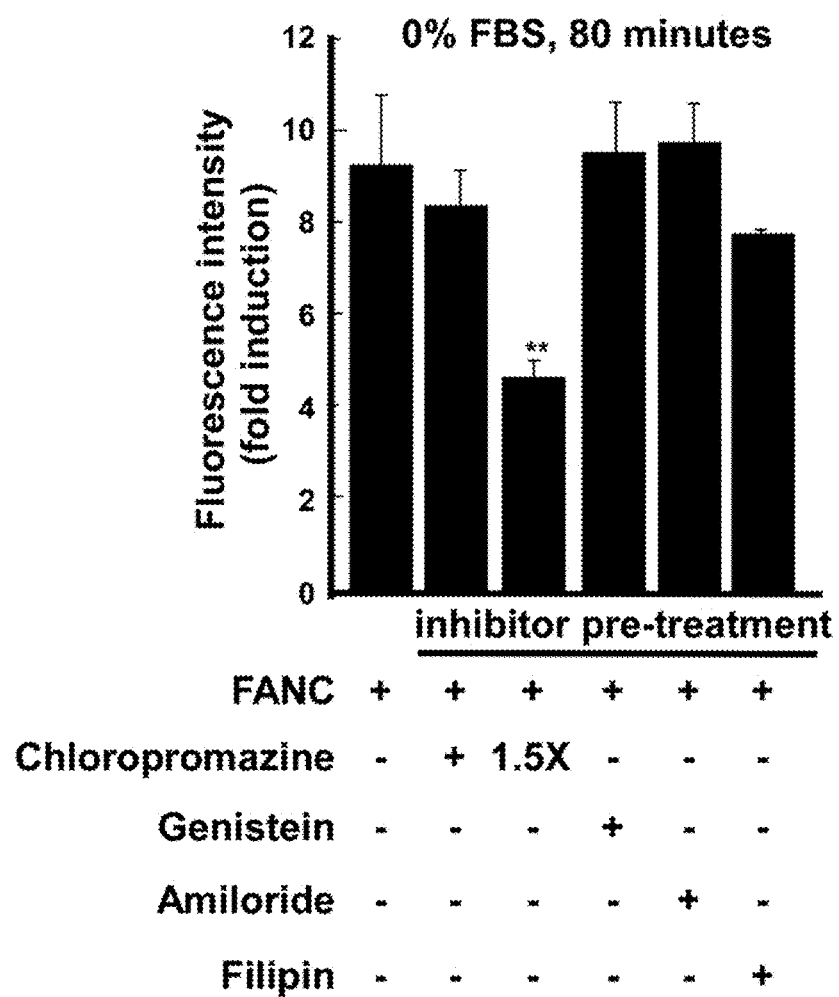
Figure 1D:
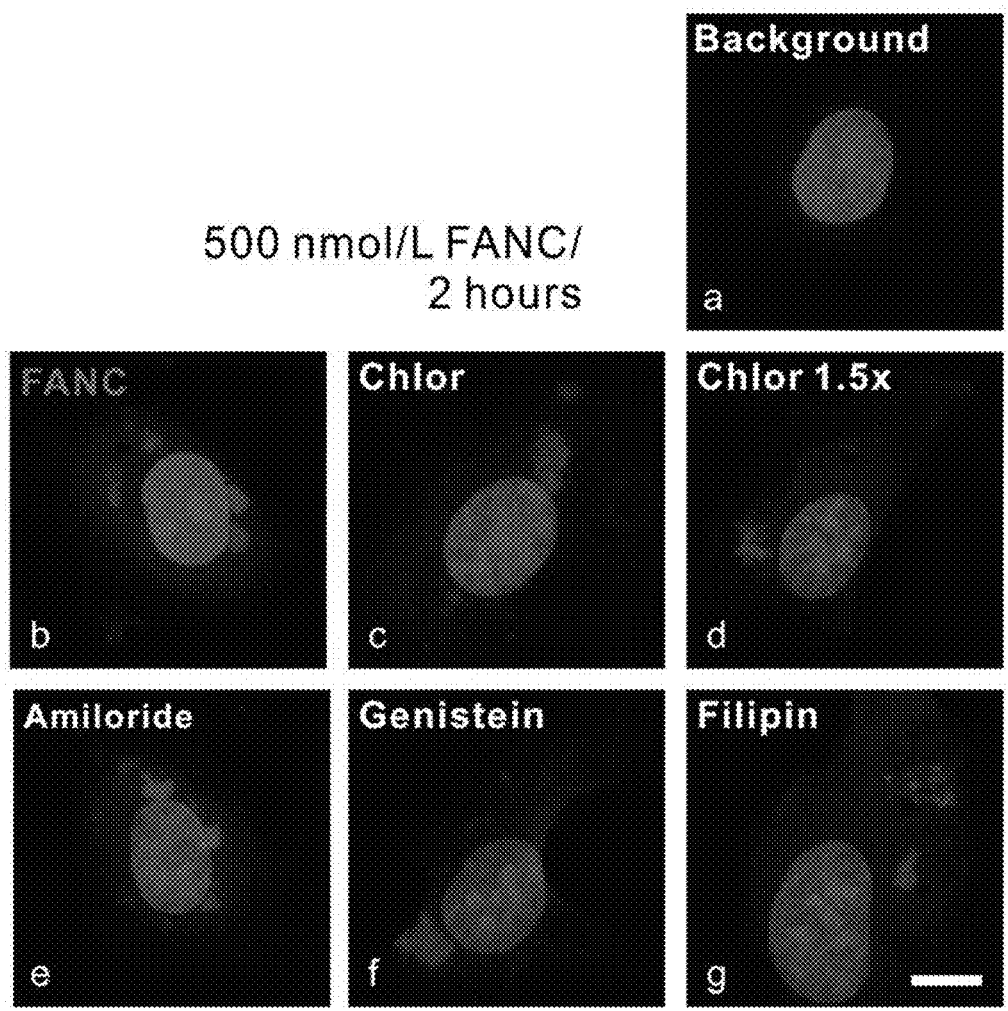

Experiment 1: Effect of Clathrin-Mediated Endocytosis on Fancs Internalization After 45 minutes of inhibitors pre-treatment (except 30 minutes of filipin treatment), FANCs were added and the incubation continued for additional 80 minutes. Thereafter, cells were subject to flow cytometry (FIGS. 1A-1D). In complete medium, chlorpromazine hydrochloride and amiloride, which respectively inhibited clathrin-dependent endocytosis and macropinocytosis, and non-clathrin endocytosis inhibitors, including genistein and filipin, had slighter effects on FANCs internalization (FIG. 1A). However, in low serum or no serum medium, internalization of FANCs was blocked by chlorpromazine hydrochloride (compared to FANCs control, 60% of decrement at 1% FBS medium and 51% of decrement at no serum medium; FIGS. 1B and 1C). Confocal microscopy showed that chlorpromazine hydrochloride treatment down-regulated the punctate fluorescence signals (FIG. 1D, Panels c-d). Short-term monitoring showed colocalization of FANCs with clathrin heavy chain (clathrin HC) in HAECs after 15 minutes of FANCs treatment. After 1 hour of FANCs incubation, enlarged and z-dimensional images indicated that punctate FANC signals were increased and enclosed with clathrin HC signals. Additional transmission electron microscopy confirmed the presence of coated pits structure at the apical membrane after 30 minutes of FANCs incubation (500 nmol/L, data is not shown), which suggests that the internalization of FANCs might be mediated by clathrin.

Experiment 2: Beneficial Effect of Fancs on Inflammation In Vitro

Figure 2A:
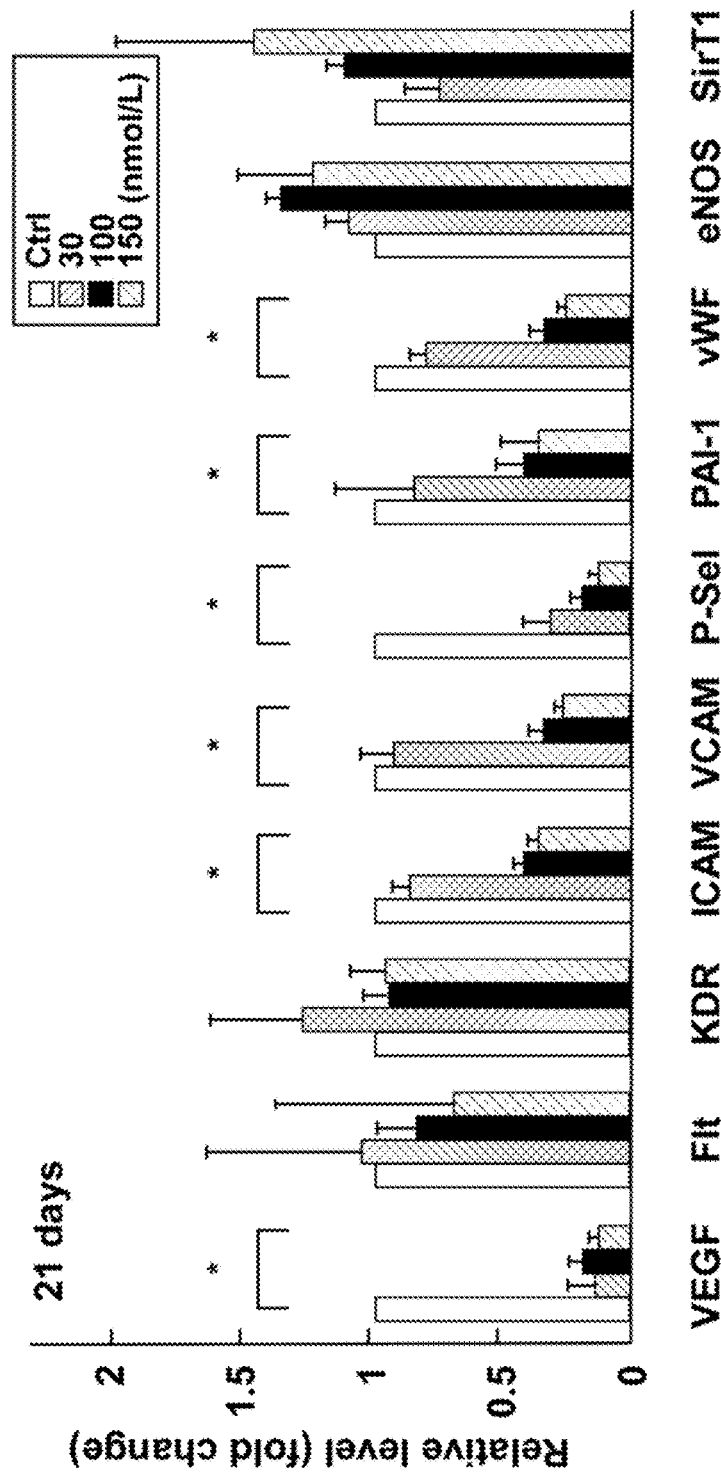
FIGS. 2A-2B are the data depicting mRNA expression profile of HAECs pre-treated with FANC for long term duration.
Figure 2B:
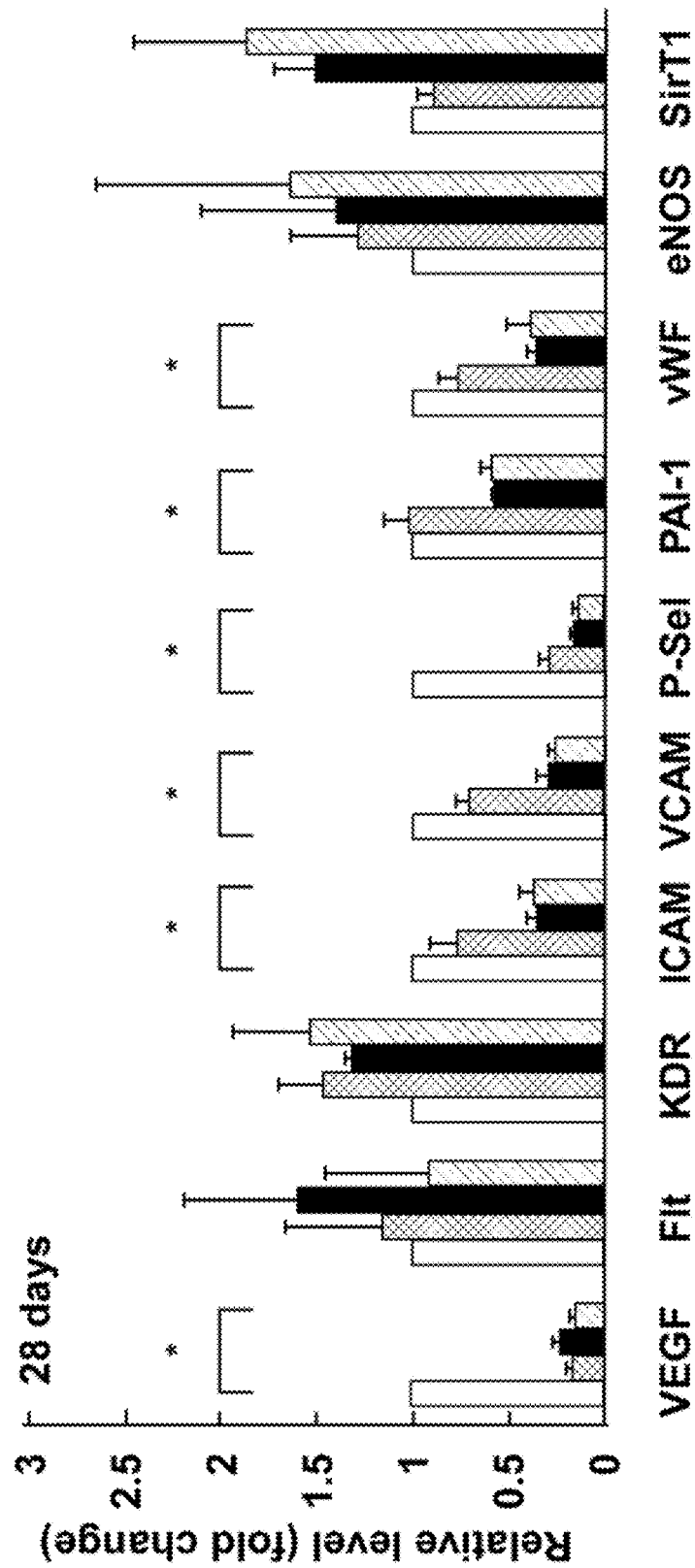

To examine cellular markers affected by FANCs, cells maintained in complete medium supplemented with FANCs were cultured for up to 4 weeks and evaluated by real-time PCR at indicated time points (21 and 28 days). The transcripts of endothelial activities involving angiogenesis, inflammation, coagulation, adhesion, growth, and vasodilation were examined. The results showed down-regulation of growth factor, adhesion molecules, and coagulatory factors in a dose-dependent manner (FIGS. 2A and 2B). It can be observed that, compared to the control groups (no FANCs treatment), the decrement of each molecule post 21 days of culture with FANCs (150 nmol/L) supplement individually is VEGF, 88%; ICAM-1 ("ICAM" in figure), 64%; VCAM-1 ("VCAM" in figure), 74%; P-selectin, 88%; PAI-1, 64%; and vWF, 75% (FIG. 2A; *, P<0.05). Further, the decrement of each molecule post 28 days of culture with FANCs (150 nmol/L) supplement is: VEGF, 87%; ICAM-1, 62%; VCAM-1, 76%; P-selectin (P-Sel in figure), 87%; PAI-1, 42%; and vWF, 62% (FIG. 2B; *, P<0.05). On the contrary, FANCs had minimal effect on the expression level of VEGF receptors, eNOS, and SirT1.

Figure 3A:
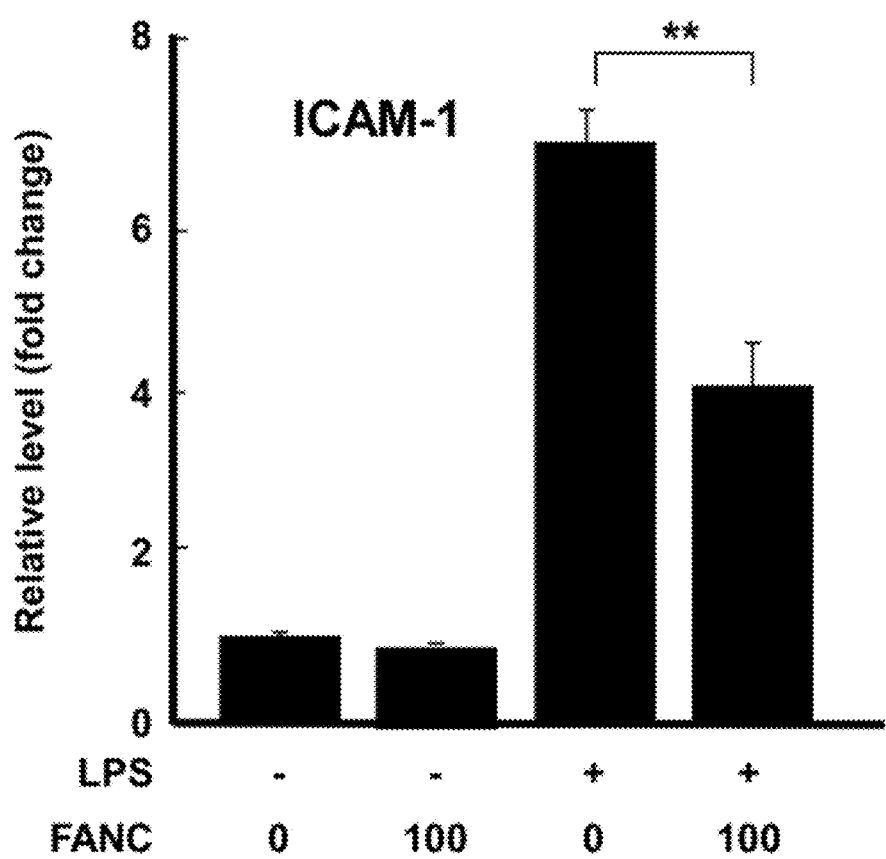
FIGS. 3A-3B are the data respectively depicting mRNA expression levels of adhesion molecules 1 (ICAM-1 in FIG. 3A; VCAM-1 in FIG. 3B) in HAECs pre-treated with FANC for short term duration (3 days) and then activated with 100 ng/ml of lipopolysaccharide (LPS, form *Escherichia. Coli* 0111:B4) overnights. Values are mean±SD of triplicate assays from 3 independent experiments. , $P<0.01$; *, $P<0.001$, compared to control group.
Figure 3B:
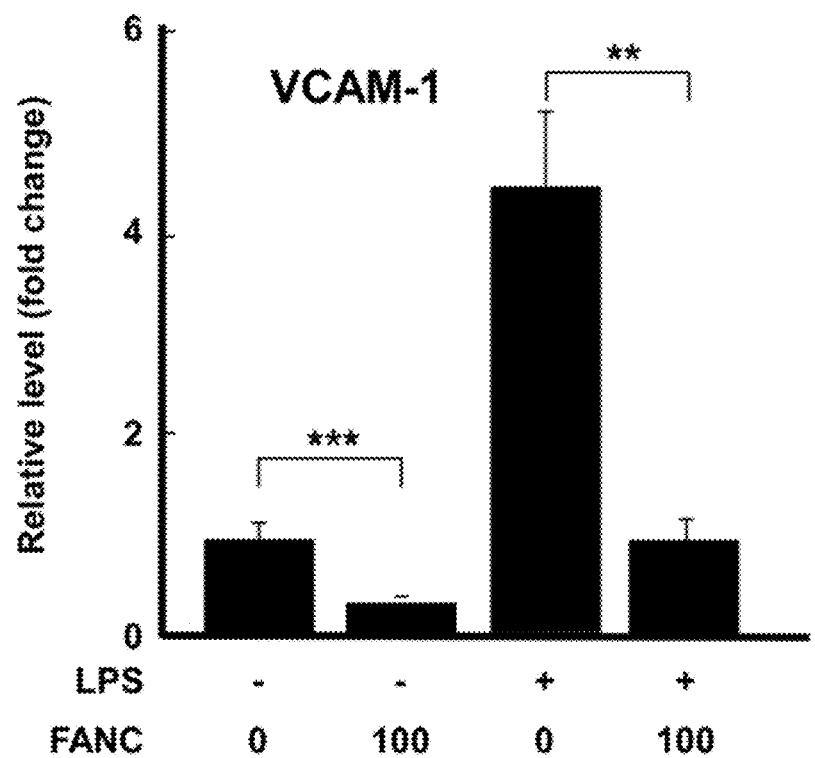
Figure 4A:
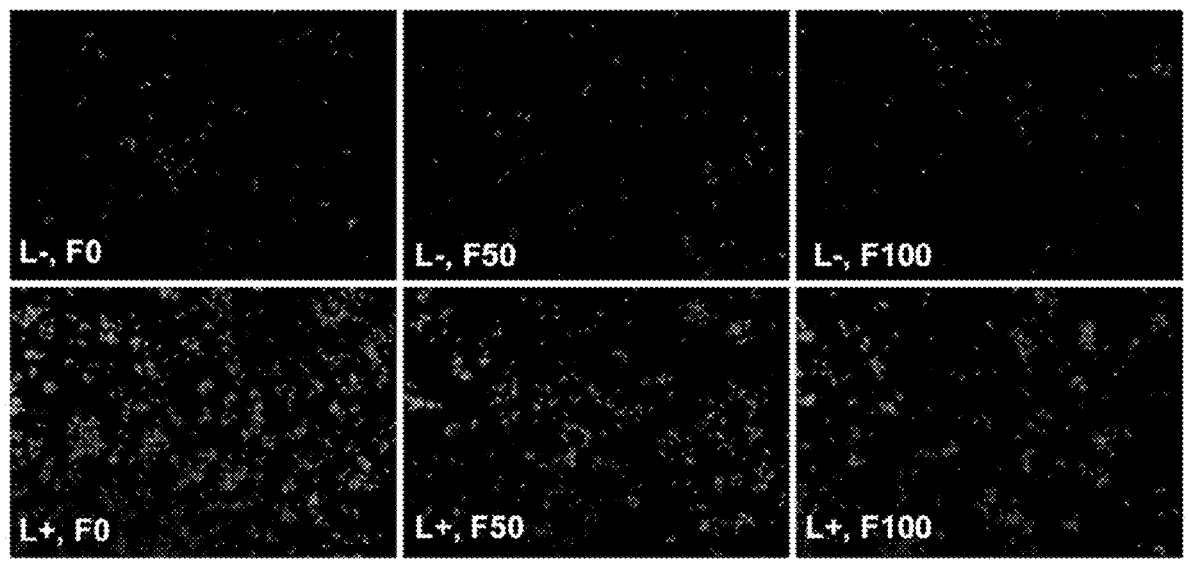
FIGS. 4A-4B are the data depicting the results of cell adhesion assay where HAECs were co-cultured with THP-1 cells.
Figure 4B:
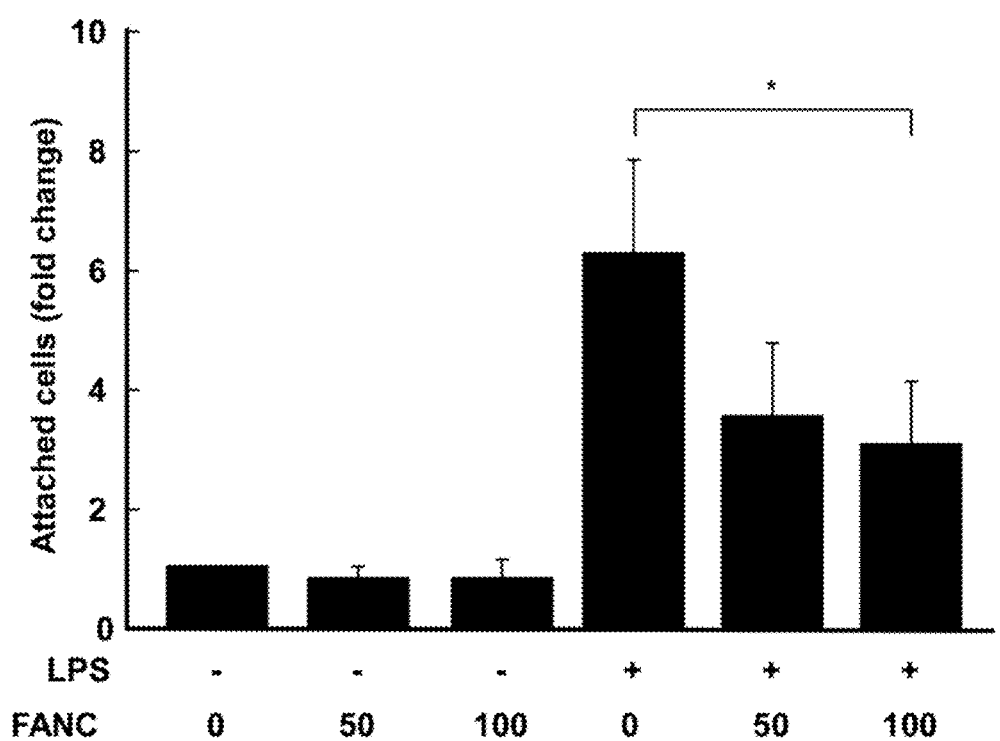

To clarify if such effects of FANCs on adhesion molecules under inflammatory status, HAECs were treated with FANCs for 3 days and then activated by LPS overnight, followed by measuring transcription levels of adhesion molecules. It can be observed that, in addition to the attenuation for long term duration, FANCs also reverted the level of adhesion molecules (ICAM-1 and VCAM-1) that were overexpressed by LPS induction in a short period (FIGS. 3A and 3B).

A cell adhesion assay was further conducted to evaluate if the reduced expression of ICAM-1 and VCAM-1 can be translated into weaker attachment behavior of leukocytes onto endothelial cells. HAECs were treated with FANCs for 3 days, activated by LPS overnight, and then co-cultured with THP-1 cells for 1 hour. The quantification data of attaching THP-1 cells on the HAECs showed that FANCs treatment resulted in a marked reduction of attached THP-1 cells.

Figure 5A:
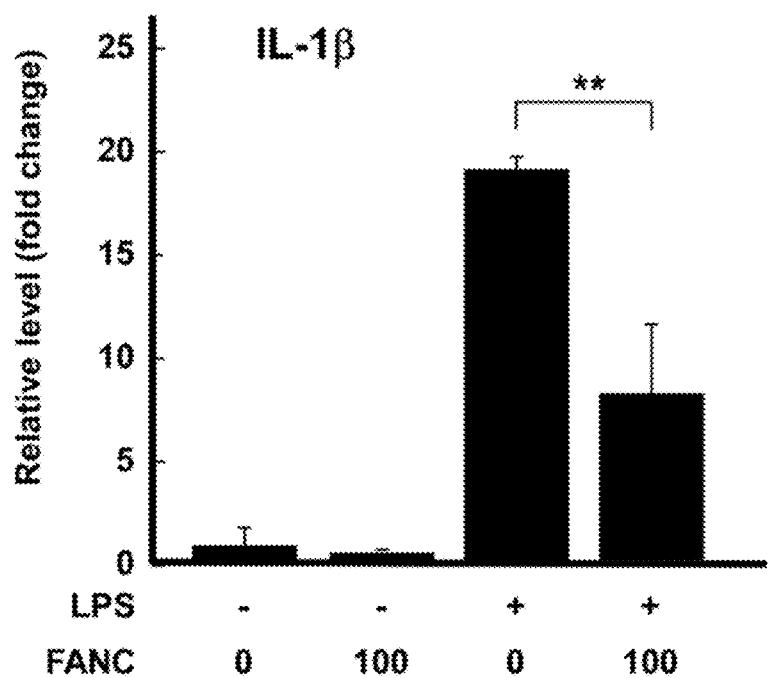
FIGS. 5A-5C are the data depicting mRNA expression levels of inflammatory cytokines: IL-1β (FIG. 5A), IL-8 (FIG. 5B), and TNF-α (FIG. 5C) in HAECs pretreated with FANCs (nM) for 3 days and then activated with LPS (100 ng/ml) overnight. Values are mean±SD of triplicate assays from 3 independent experiments. *, $P<0.05$; , $P<0.01$; *, $P<0.001$.
Figure 5B:
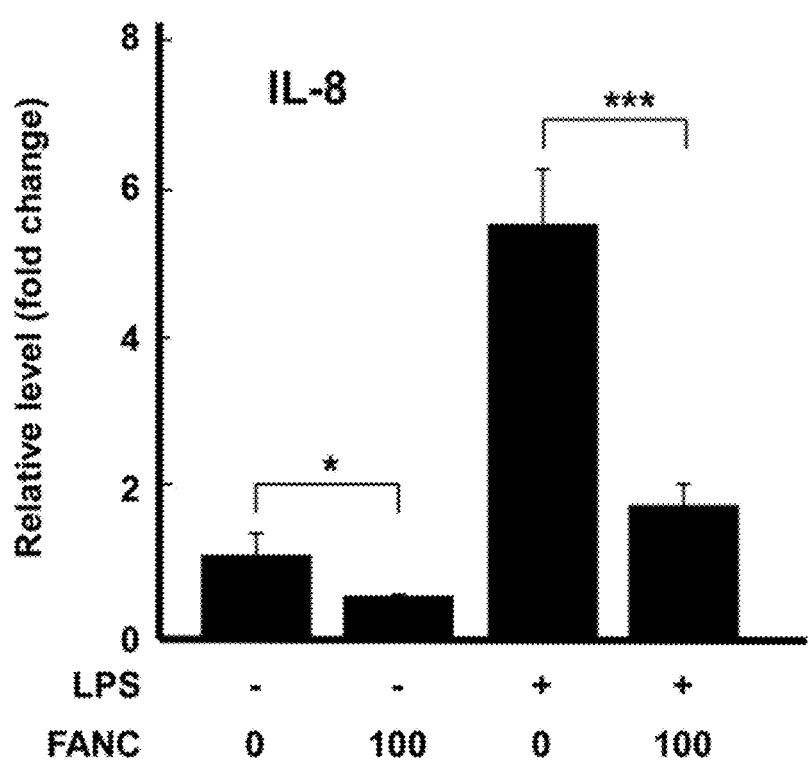
Figure 5C:
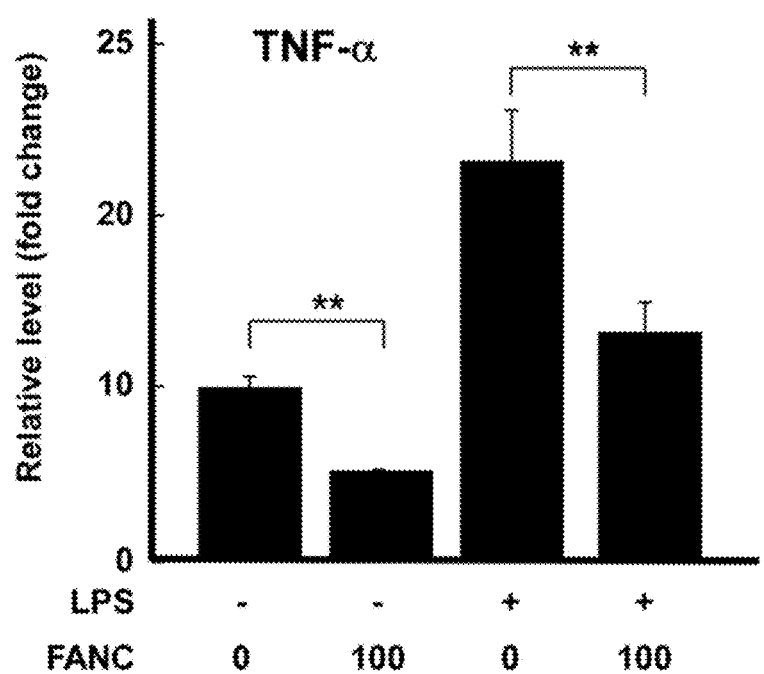

In addition to adhesion molecules, the effects of FANCs on the expression of inflammatory cytokines in endothelial cells were studied. For this purpose, HAECs were treated with FANCs for 3 days and then activated by LPS overnight. The expression levels of inflammatory cytokines: IL-1β, IL-8 and TNF-α were analyzed after incubation. The results showed that all three molecules were significantly up-regulated by LPS, while the increment was attenuated by FANCs treatment (FIGS. 5A-5C).

Experiment 3: Beneficial Effect of Fancs on Inflammation In Vivo

Figure 6:
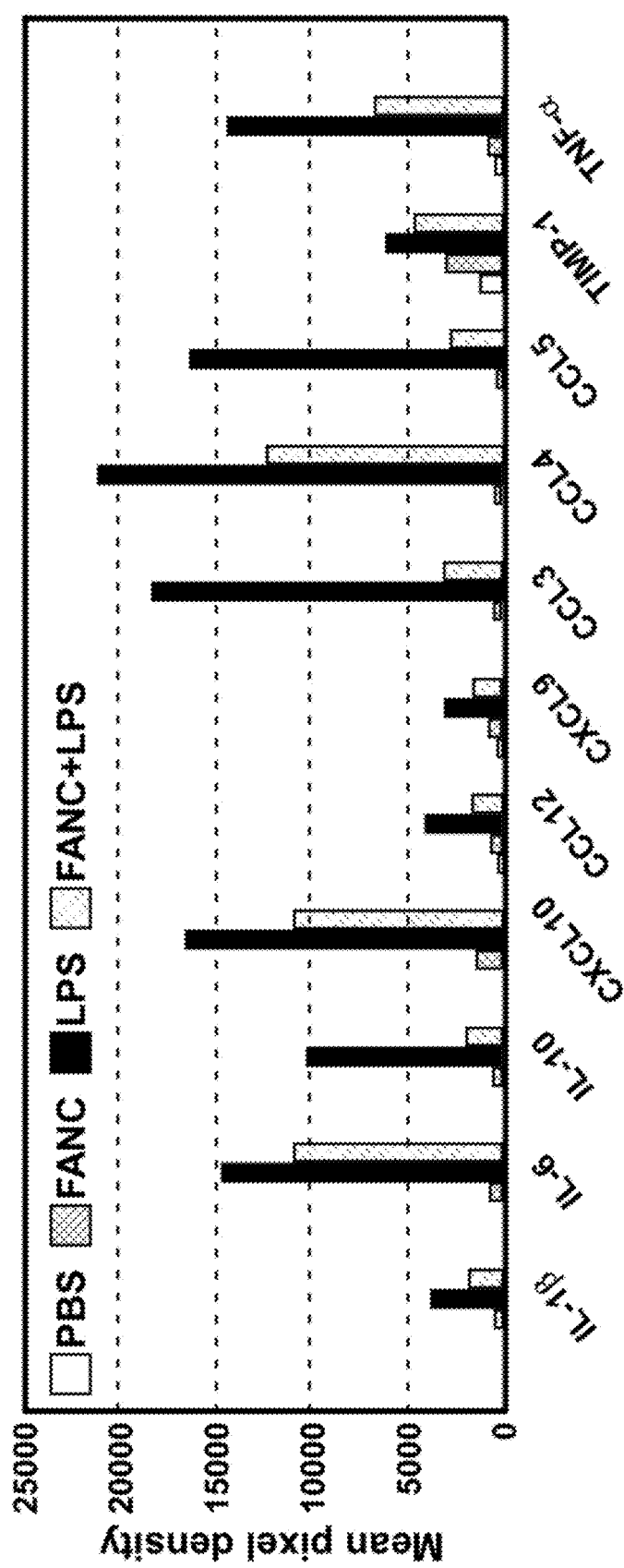
FIG. 6 is the data depicting the effect of FANC on alleviating inflammation in mice intraperitoneally injected with PBS, FANC (100 nM), LPS (10 mg/Kg), and FANC+LPS, respectively, for 2 hours. N=3 for each group.

Animal studies were conducted for the purpose of clarifying the anti-inflammatory effect of FANCs in vivo. Adult male mice were grouped in four, and each group was intraperitoneally administered by phosphate-buffered saline (PBS), FANCs (100 nM), LPS, and FANCs plus LPS (10 mg/Kg) for 2 hours. Equal amount of sera was harvested and pooled for determination of pro-inflammatory and/or inflammatory molecules, which includes IL-1β, IL-6, IL-10, CXCL9, CXCL10, CCL3, CCL4, CCL5, CCL12, TIMP-1 and TNF-α by antibody arrays (ARY006, R&D systems, USA). It can be observed that, compared to a marked increase of the pro-inflammatory and/or inflammatory molecules by LPS administration alone, the increments of such molecules, especially IL-1β, IL-10, CCL4, CCL5, and TNF-α were attenuated in the mice by treating with both LPS and FANCs (FIG. 6).

In conclusion, the present disclosure demonstrated that the DHLA coated gold nanoclusters can lower the expression of certain pro-inflammatory molecules, such as adhesion molecules, coagulator factors and even inflammatory cytokines in vitro and in vivo. Accordingly, the present method comprising administering the DHLA coated gold nanoclusters and/or a pharmaceutical composition thereof may provide a potential means to effectively prevent or treat a subject from being suffered inflammation-related diseases.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating an inflammatory disease in a subject, comprising administering to the subject an effective amount of a dihydrolipoic acid (DHLA) coated gold nanocluster about 0.1 to 20 nm in diameter, and an endocytosis inhibitor, wherein,
    the DHLA coated gold nanocluster consists of a gold nanocluster formed by a plurality of gold nanoparticles, and a plurality of DHLA coated on the gold nanocluster; and
    the administration of the DHLA coated gold nanocluster reduces the expression of vascular endothelial growth factor (VEGF), intercellular adhesion molecule 1 (ICAM-1), vascular cell adhesion protein-1 (VACM-1), P-selectin, plasminogen activator inhibitor-1 (PAI-1), von Willebrand factor (vWF), tumor necrosis factor alpha (TNF-α), interleukin-8 (IL-8), and/or interleukin-1β(IL-1β) in the subject.

2. The method of claim 1, wherein the DHLA coated gold nanocluster is about 1 to 2 nm in diameter.

3. The method of claim 1, wherein the inflammatory disease is any of a cardiovascular disease, an inflammatory bowel disease, organ transplant rejection, lupus, an autoimmune disorder, a radiation-induced injury, cancer, a burn, trauma, a rheumatic disorder, a renal disease, an allergic disease, an infectious disease, an ocular disease, a skin disease, a gastrointestinal disease, a hepatic disease, cerebral edema, sarcoidosis, thrombocytopenia, or a spinal cord injury.

4. The method of claim 3, wherein the inflammatory disease is the cardiovascular disease.

5. The method of claim 4, wherein the cardiovascular disease is angina pectoris, atheroma, atherosclerosis, arteriosclerosis, congestive heart failure, coronary heart disease, cardiomyopathy, myocardial infarction, stroke, ischemic conditions, ischemic cardiomyopathy, patent ductus arteriosus, high blood pressure, pulmonary hypertension, peripheral artery disease, coronary artery disease, coronary artery spasm, or pericarditis.

6. The method of claim 1, wherein the subject is a human.

7. The method of claim 1, wherein the endocytosis inhibitor is administered before, or concurrent with the administration of the DHLA coated gold nanocluster.

8. The method of claim 1, wherein the effective amount of the DHLA coated gold nanocluster is about 1 to 15 nM per day.

9. The method of claim 8, wherein the effective amount of the DHLA coated gold nanocluster is about 3 to 12 nM per day.

10. The method of claim 9, wherein the effective amount of the DHLA coated gold nanocluster is about 6 to 10 nM per day.

11. A method for reducing the expression of a pro-inflammatory molecule in a cultured cell, comprising contacting the cultured cell with about 1 to 1,000 nM of a dihydrolipoic acid (DHLA) coated gold nanocluster about 0.1 to 20 nm in diameter, and an endocytosis inhibitor, wherein,
- the DHLA coated gold nanocluster consists of a gold nanocluster formed by a plurality of gold nanoparticles, and a plurality of DHLA coated on the gold nanocluster; and
- the pro-inflammatory molecule is selected from the group consisting of vascular endothelial growth factor (VEGF), intercellular adhesion molecule 1 (ICAM-1), vascular cell adhesion protein-1 (VACM-1), P-selectin, plasminogen activator inhibitor-1 (PAI-1), von Willebrand factor (vWF), tumor necrosis factor alpha (TNF-α), interleukin-8 (IL-8), and interleukin-1β(IL-1β).

12. The method of claim 11, wherein the DHLA coated gold nanocluster is about 1 to 2 nm in diameter.

13. The method of claim 12, wherein the cultured cell is selected from the group consisting of human aortic endothelial cell (HAEC), human epithelial cell, human coronary artery endothelial cell (HCAEC), and human endothelial progenitor cell (HEPC).

14. The method of claim 11, wherein the cultured cell contacts the endocytosis inhibitor before or concurrent with the contact of the DHLA coated gold nanocluster.

* * * * *